US006291248B1

(12) United States Patent
Haj-Ahmad

(10) Patent No.: US 6,291,248 B1
(45) Date of Patent: *Sep. 18, 2001

(54) NUCLEIC ACID PURIFICATION AND PROCESS

(75) Inventor: Yousef Haj-Ahmad, St. Catharines (CA)

(73) Assignee: Norgen Biotek Corporation, Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/658,808

(22) Filed: Sep. 11, 2000

Related U.S. Application Data

(63) Continuation of application No. 09/475,430, filed on Dec. 30, 1999, now Pat. No. 6,177,278.

(30) Foreign Application Priority Data

Apr. 23, 1999  (CA) .................................. 2270106

(51) Int. Cl.[7] ............................ G01N 33/00; C12M 1/34; C07H 21/02

(52) U.S. Cl. ..................... 436/94; 435/287.2; 536/23.1; 536/24.3

(58) Field of Search .............................. 435/6, 94, 287.2; 536/23.1, 24.3, 24.33; 436/94

(56) References Cited

U.S. PATENT DOCUMENTS 5,464,765 * 11/1995 Coffee et al. .................. 435/172.3

* cited by examiner

Primary Examiner—Bradley L. Sisson
(74) Attorney, Agent, or Firm—Fulbright & Jaworski, LLP

(57) ABSTRACT

The invention disclosed is particularly directed to a process for the purification of DNA, and is especially useful for the isolation of biologically active plasmid DNA. The process is initiated by binding the DNA to silicon carbide particles, either in the presence or absence of chaotropic agents. The bound DNA is subsequently eluted from the resin in low salt buffer or water. The resulting purified DNA is substantially free of proteins and is shown to be biologically active. The scope and diversity of the process is demonstrated here since this process can be used for the isolation of RNA and genomic DNA as well as the purification of PCR products and isolation of DNA from agarose gel slices.

18 Claims, 7 Drawing Sheets

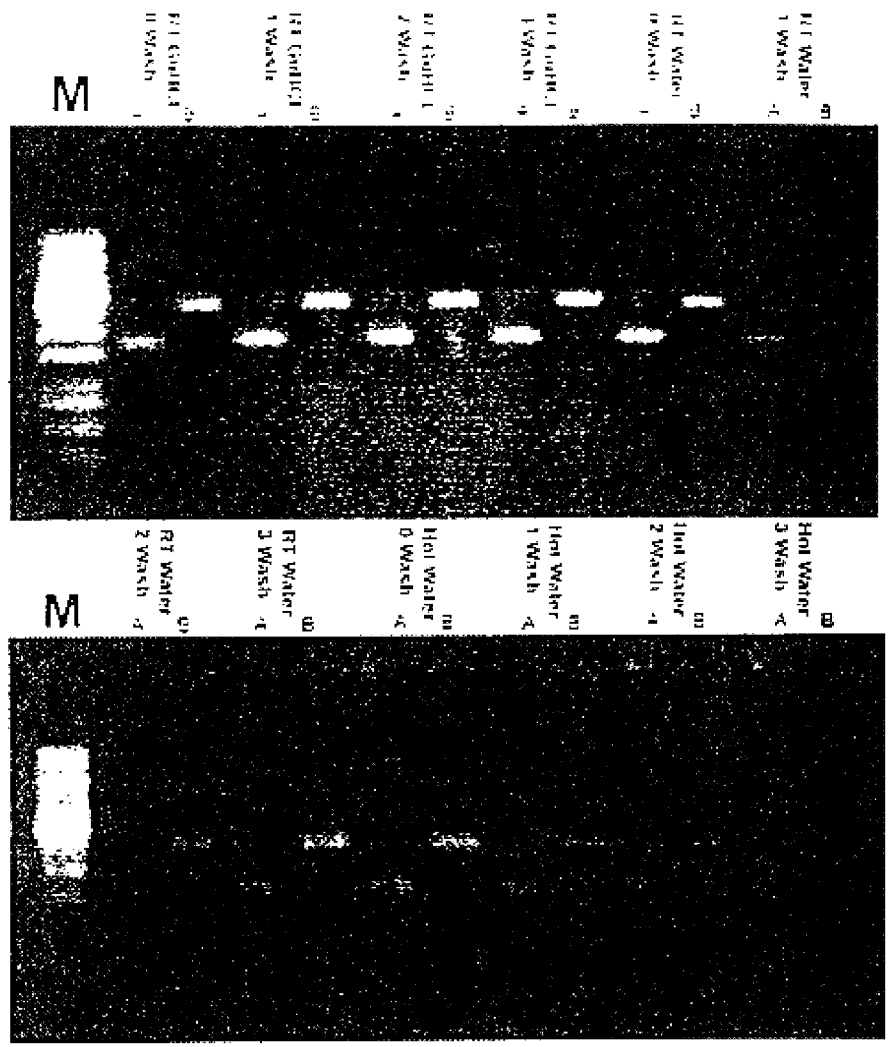

Figure 1.0: Effect of pre-washing Silicon Carbide 1000 (SiC 1000) on quality of plasmid DNA isolated. SiC 1000 was treated before use with a variety of types and frequencies of washes. pUC 19 plasmid DNA was then isolated with the washed resin and digested with the restriction enzyme Hind III. Type and frequency of wash are indicated above each pair of lanes. "A" lanes show undigested pUC 19. "B" lanes show pUC 19 digested with Hind III. "M" lane is the marker lane. RT = room temperature. GuHCl = 1 M Guanidine Hydrochloride.

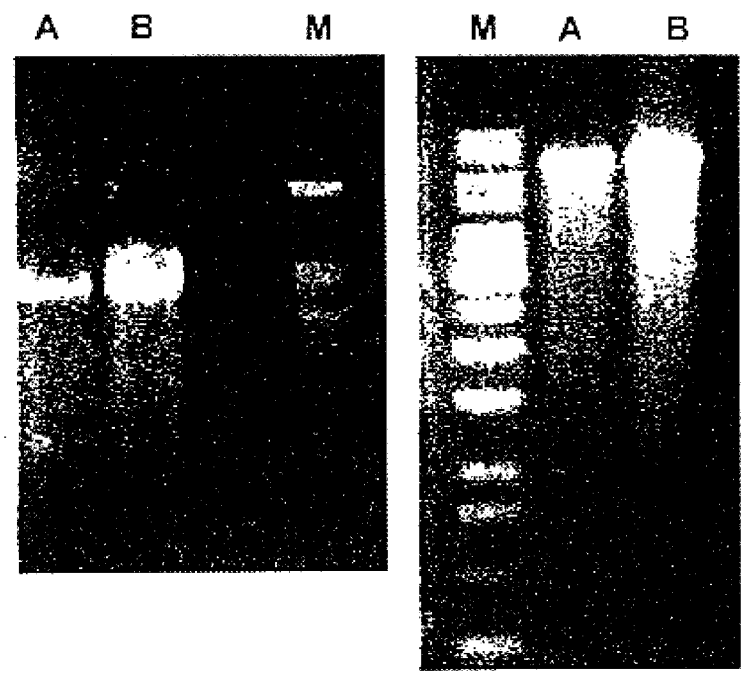

Figure 2.0: Isolation of DNA fragments from agarose gel slices. pCMV beta (7164 bp) DNA was digested with the restriction enzyme *Hind* III which yielded the single linear fragment of pCMV beta DNA 7164 bp in length (left side photo). The DNA present in lanes A and B was isolated from agarose slices cut from the gel as described in Example 5. The isolated DNA was subsequently run on a second agarose gel and photographed to ascertain the recovery (right side photo). "M" lanes are marker lanes.

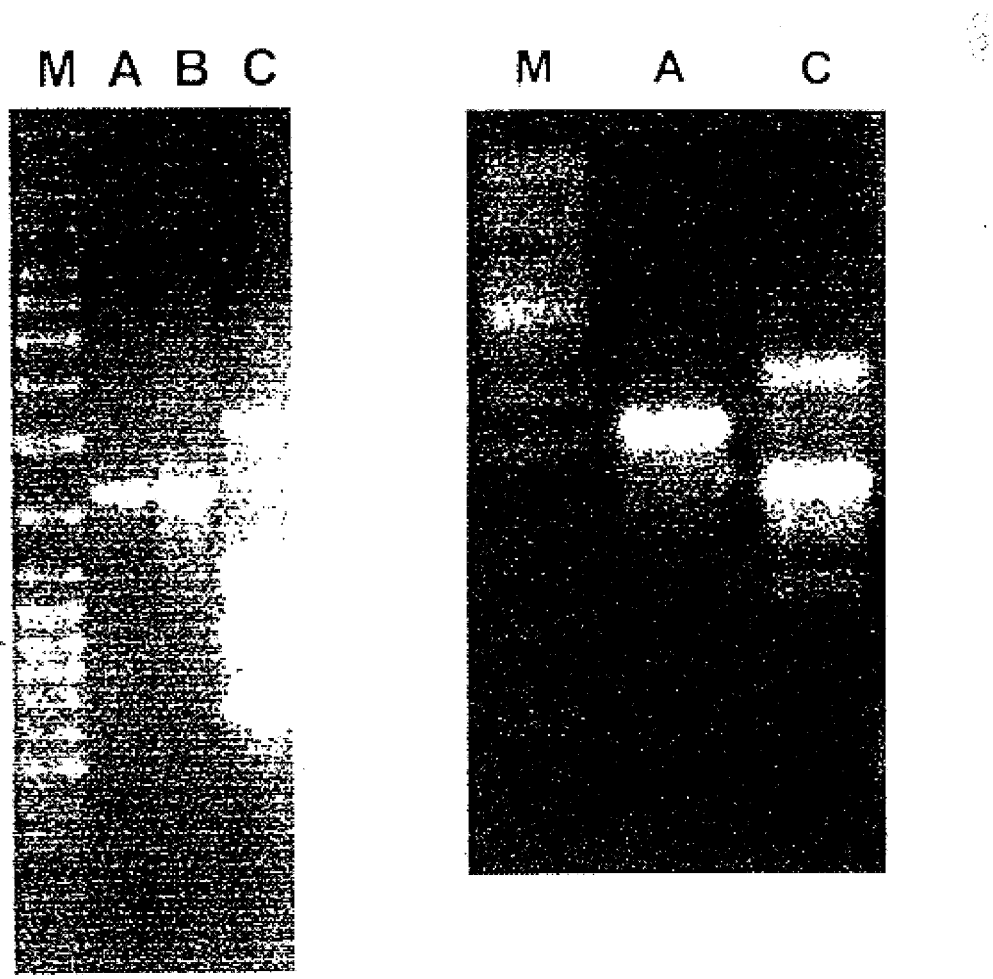

Figure 3.0: PCR Product Isolation. PCRs were carried out and a sample of the reaction products were loaded onto agarose gel for analysis (left photo). PCR samples A and C were then used to test the ability of silicon carbide to isolate PCR fragments as described in Example 6. The isolated PCR fragments were then run on a second agarose gel for comparison (right photo). "M" represents a marker lane.

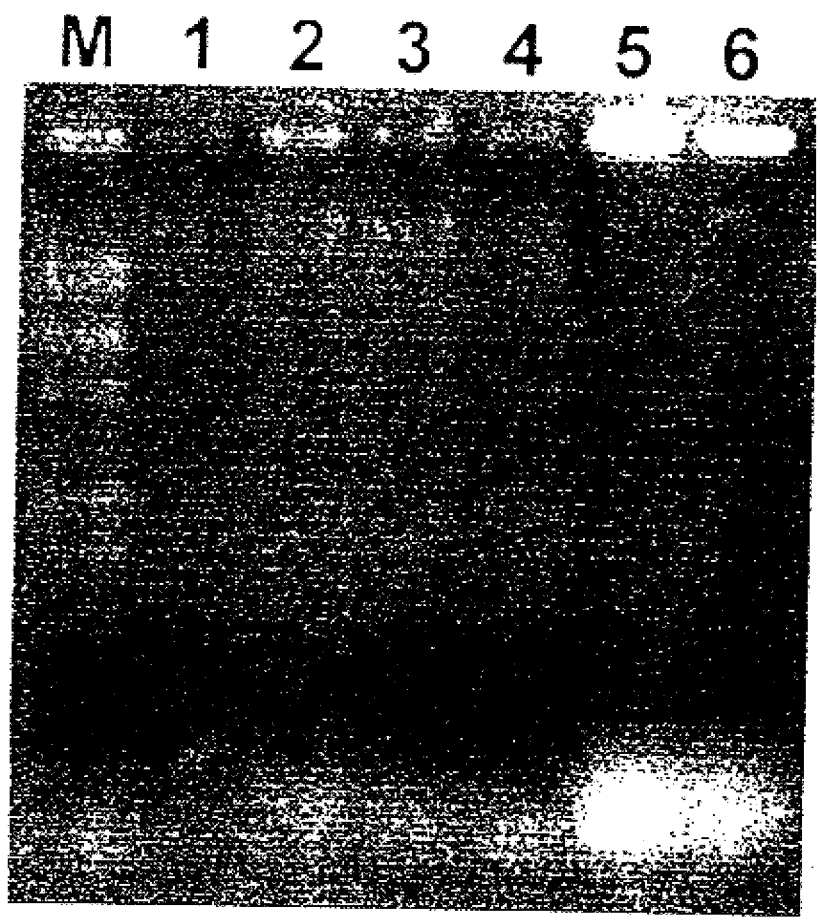
Figure 4.0: Isolation of Genomic DNA from *E. coli* DH5α. Lanes 1-4 show four samples of genomic DNA isolated as described in Example 7. Lanes 5 and 6 show genomic DNA isolated by isopropanol precipitation for comparison. Lane "M" is a marker lane.

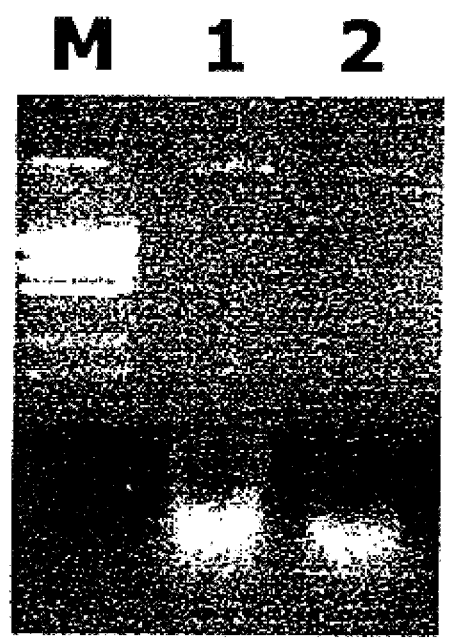
Figure 5.0: Binding of RNA to silicon carbide 1000. Two samples of RNA were isolated using silicon carbide 1000 and run an agarose gel. Lanes 1 and 2 show RNA samples. Lane "M" is a marker lane.

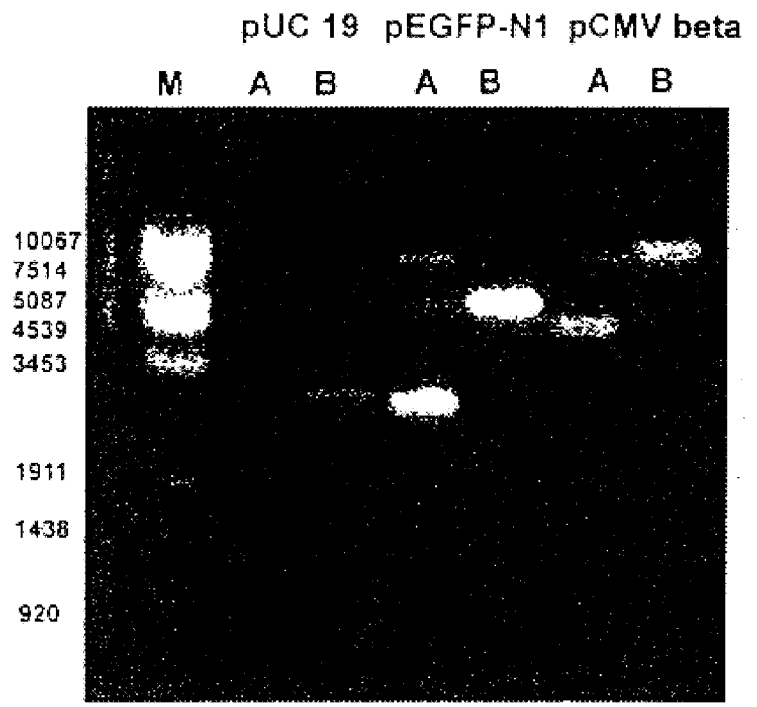
Figure 6.0: Isolation of a range of plasmid sizes using silicon carbide and digestion with restriction enzymes. "A" lanes show undigested samples. "B" lanes show digested samples. Plasmids are indicated at top of figure. "M" lane is the marker lane. pUC 19 was digested with *Hind* III. pEGFP-N1 was digested with *Bam* HI. pCMV beta was digested with *Hind* III.

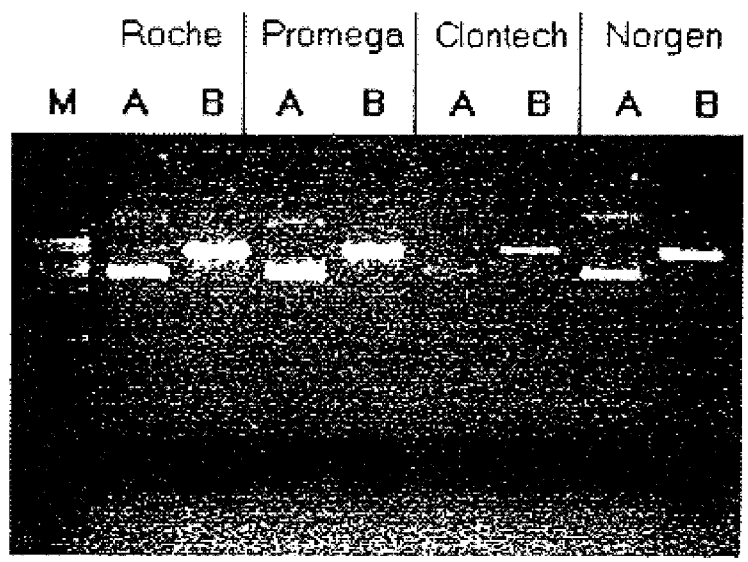
Figure 7.0: Comparison of digestions of plasmid pCMV beta (7164 bp) purified using three commercial DNA purification kits and silicon carbide 1000. "A" lanes show undigested pCMV beta while "B" lanes show pCMV beta digested with *Hind* III. Lane "M" is a marker lane. Commercial kits used for purification are listed along top of figure.

NUCLEIC ACID PURIFICATION AND PROCESS

This is a continuation of Ser. No. 09/475,430, filed Dec. 30, 1999, now U.S. Pat. No. 6,177,278.

FIELD OF THE INVENTION

The invention relates to methods for nucleic acid purification and in particular to purification methods wherein nucleic acid is removed from a solution by binding it to an inert carrier.

BACKGROUND OF THE INVENTION

It is well known that the purity of DNA and RNA used in scientific and medical research is a critical factor in the success of such research. For example, gene transfer experiments in cell cultures, immunization using DNA-based vaccines and DNA sequencing projects are a few of the research areas where DNA of high purity is essential for project success. Sufficiently pure DNA is not normally attainable using traditional methods of DNA isolation. Furthermore, the process of isolating and purifying DNA is a major rate-limiting step in molecular biology. Traditional methods of isolating pure DNA have typically involved toxic chemicals such as phenol/chloroform extraction procedures, and very long centrifugation times such as in Cesium Chloride banding procedures. Not only are such procedures slow and costly, they also represent a health risk to laboratory staff and demand the usually expensive disposal of hazardous chemicals. Furthermore, despite careful preparation, DNA prepared using these methods may not always be free of RNA, proteins and chromosomal DNA.

As a result, the demand for safe, high quality and rapidly obtainable DNA preparations grown in bacteria such as *E. coli* has risen steadily and a variety of commercial kits have become available to meet a wide range of DNA purification needs. However, a number of these kits suffer from disadvantages, ranging from high price to failing to produce the desired quality and yield.

It is known that DNA will bind to silicon-containing materials such as glass slurries and diatomaceous earth. In fact, DNA purification kits are available which make use of these silicon-containing substances. For example, Bio 101 offers the GENECLEAN™ kit which makes use of a glass slurry and sodium iodide (binding buffer) and BioRad™ offers a plasmid purification kit using diatomaceous earth (Celite™) suspended in guanidine hydrochloride buffer.

U.S. Pat. Nos. 5,503,816 and 5,525,319 and 5,693,785 by Woodard et al. describe the use of silicate compounds for DNA purification. The disadvantage with these materials is that the required silicate material is not readily commercially available in the appropriate form, and typically must be prepared requiring additional time for DNA isolation procedures.

U.S. Pat. Nos 5,438,129 and 5,625,054 describe DNA isolation procedures which utilize flourinated Celite™, flourinated silicon dioxide or flourinated aluminum hydroxide. These inventions require the use of toxic chemicals to create the flourinated surfaces to which the DNA will bind. In addition, chaotropes which are also toxic, are still required for these procedures.

U.S. Pat. Nos. 5,534,054 and 5,705,628 both disclose methods for isolating DNA which do not require the use of toxic chaotropic agents. The former patent discloses the use of silicon tetrahydrazide for the purification of DNA, but the preparation of the binding material requires the use of toxic chemicals which can lead to conditions such as nausea and temporary blindness. The latter of the patents relates to a non-specific, reversible binding of DNA particles using magnetic microparticles.

SUMMARY OF THE INVENTION

It is now an object of the present invention to provide a method for the purification of DNA using an inexpensive commercially available material, that does not require the use of chaotropic agents, and rapidly yields high quality preparations of DNA.

Accordingly, the invention provides the use of silicon carbide for binding a nucleotide polymer.

The invention further provides a method for purifying nucleic acid from a sample including the steps of provding a silicon carbide carrier for binding nucleic acids;

adding the nucleic acid containing sample to the carrier for binding nucleic acid in the sample to the silicon carbide;

separating the silicon carbide from the liquid;

eluting from the silican carbide the nucleic acid bound thereto.

The present invention provides an economical nucleic acid purification method using silicon carbide compounds, preferably commercially available industrial quality silicon carbide. A typical industrial preparation of silicon carbide (SiC) which is applicable for use in the purification is composed of 97.8% silicon carbide and small amounts of silicon dioxide, silicon, iron, aluminum and carbon. This substance is affordable and readily available as a DNA-binding material. Silicon carbide is available in a variety of grit sizes or grades, and each grade has a different capacity for binding nucleic acids (all obtained through Ritchey Supply Ltd. Mississauga, Ontario). Any grade of SiC used in the method according to the present invention is preferably suspended as a 15% (w/v) slurry, preferably in either distilled water or a solution of guanidine hydrochloride.

Another preferred process of the invention is used for the purification of plasmid DNA from a sample and involves the following steps:

1. Immobilizing the DNA in the sample onto silicon carbide 1000 in the presence or absence of a binding buffer;
2. Separating the silicon carbide with the DNA immobilized thereon from the sample;
3. Washing the subsequent silicon carbide-bound DNA with an ethanol-containing buffer;
4. Removing the ethanol-containing buffer; and
5. Eluting the DNA in a low salt buffer (TE) or in water.

BRIEF DESCRIPTION OF THE DRAWINGS

FIG. 1 shows an agarose gel illustrating the effect of pre-washing silicon carbide.

FIG. 2 shows a result of using the invention for the isolation of DNA fragments from agarose gel slices.

FIG. 3 is a picture of agarose gel demonstrating the recovery of PCR products using the invention.

FIG. 4 is an agarose gel photograph showing the improved isolation of *E. Coli* DH5α genomic DNA using silicon carbide.

FIG. 5 shows an agarose gel indicating isolation of RNA using the process of the invention.

FIG. 6 is an agarose gel showing a range of plasmids, or different sizes isolated using the invention.

FIG. 7 is an agarose gel comparing the quality of the DNA isolated using an embodiment of the invention.

DETAILED DESCRIPTION OF THE PREFERRED EMBODIMENT

All grades of silicon carbide tested were able to purify plasmid DNA. Furthermore, all molarities of guanidine hydrochloride (including 0M or simply distilled water) appeared to be sufficient to allow the binding of DNA to silicon carbide. However, two trends were evident:

1. Finer grade silicon carbide (i.e. smaller grit size, such as SiC 1000) appeared to give higher yields of bound plasmid DNA; and
2. A high concentration of guanidine hydrochloride (5–7M) produced higher plasmid yield. Thus most of the examples illustrated in this report involve the use of SiC 1000 suspended in a 5–7 molar guanidine hydrochoride solution.

The primary objective of the exemplary methods carried out was the purification of plasmid DNA from bacterial lysates by immobilizing DNA onto silicon carbide 1000 in the presence of a high salt binding buffer such as guanidine hydrochloride. The bound DNA was subsequently eluted into a low salt buffer such as TE buffer or water.

Generally, the first step in the isolation of plasmid DNA, using the preferred method of this invention, is the pelleting of 1–3 ml of an overnight bacterial culture comprised of host cells containing a plasmid of interest. This is followed by the resuspension of the bacterial pellet in a buffer of Tris HCl and EDTA including 100 µg/ml RNase A. The presence of RNase A in this buffer significantly reduces the amount of RNA generally observed in the final plasmid preparation. The cells are then lysed under alkaline conditions (NaOH and sodium dodecyl suplhate (SDS)) until the tubes containing resuspended cells are largely clear (generally not longer than five minutes is required). The solutions are then neutralized using 2M potassium acetate and centrifuged for at least 10 minutes. After this stage, the solution containing plasmid DNA is brought into contact with the silicon carbide and binding of plasmid to SiC occurs while proteins and other macromolecules generally do not bind. Subsequently, during the wash steps that follow, plasmid DNA remains bound to SiC while proteins are removed as wash is aspirated or flows through a spin column filter. After generally two rounds of washing, the resin bed (in a spin filter column) or resin pellet (in a centrifuge tube) is washed with low salt buffer (TE) or water generally warmed to 65° C. to elute the plasmid DNA. Larger volumes of elution buffer will tend to release more DNA from silicon carbide, however, this also tends to result in much lower concentrations of final DNA preparation. Also, two rounds of smaller elution volumes tends to elute more DNA than one large elution volume. For example, eluting two times with 50 µl each time rather than once with 100 µl tends to yield larger quantities of plasmid DNA.

The process of plasmid DNA isolation and the isolation of other nucleic acids is further illustrated with the following examples. These examples are designed to illustrate the scope and diversity of the invention but are not intended to limit the range of the invention. Indeed, not all possible examples are presented here.

Silicon Carbide is a dark grey, crystalline substance which is insoluble in water, acids and alkalines. Commercial preparations of silicon carbide can be obtained, wherein they are typically composed of greater than 98% SiC with smaller amounts of carbon (C), silicon (Si), silicon dioxide ($SiO_2$), and iron (Fe) also present. Silicon carbide is also available in a variety of grit sizes or grades. One preferred embodiment of the invention utilizes a grade of silicon carbide known as the 1000 grade with an average particle size of 4.5 microns. The silicon carbide used was manufactured by EXOLON ESK (Tonawanda, N.Y., USA) and distributed through Ritchey Supply Ltd (Mississauga, Ontario, Canada).

EXAMPLE 1

Preparation of Silicon Carbide 1000 Slurry

In a preferred embodiment of the invention a 15% weight/volume (w/v) slurry of silicon carbide 1000 grade grit is prepared in either distilled water or a binding buffer of guanidine hydrochloride. In this preparation silicon carbide is sterilized using an autoclave and subsequently measured without any wash or refinement of the commercial silicon carbide preparation. This prepared silicon carbide resin is then added to the liquid in which it is to be suspended, typically either distilled water or a 7M guanidine hydrochloride solution. For larger stale trials a 15% (w/v) suspension of silicon carbide in solution was typically prepared by adding 15 grams of the sterilized silicon carbide to 100 ml of solution whereas for smaller scale trials the 15% silicon carbide suspension would be prepared by adding 1.5 grams of the silicon carbide to 10 ml of solution. Slurries produced in this manner were mixed well prior to any use in purification protocols and stored at room temperature when not in use.

EXAMPLE 2

Plasmid DNA Purification Protocol

There are different protocols which can be followed for the purification of plasmid DNA using a purification process in accordance with the invention and as binding agent a slurry as described herein. These protocols could involve the use of a pelleting step, or a spin column. The composition of the buffers used in the investigation of preferred embodiments of this invention were as set out below:

1. Cell Resuspension Solution
   50 mM Tris-HCl, pH 7.5
   10 mM EDTA
   100 µg/ml RNase A (ribonuclease A, DNase-free)
2. Cell Lysis Solution
   0.2 M NaOH
   1% SDS (sodium dodecyl sulfate)
3. Neutralization Solution
   2 M Potassium Acetate, pH 4.8
4. Wash Solution
   20 mM Tris HCl, pH 7.5
   5 mM EDTA
   50 % EtOH (ethanol)
5. TE Buffer
   10 mM Tris HCl
   1 mM EDTA In order to purify *E. coli* plasmid DNA the initial step is the production of a cleared lysate from, typically 1.0–3.0 ml, of a culture of *E. coli*. The bacterial culture is pelleted by centrifugation at 14,000 rpm for 1 minute, and the supernatant is then removed. Approximately 250 µl of cell resuspension solution is added to the pellet, which is then resuspended by vortexing vigorously. Once the cells have been resuspended, 250 µl of cell lysis solution is added to the suspension, which is then mixed by several gentle inversions, but without resort to a vortex. The resulting mixture can then be incubated for up to 5 minutes at 37° C. until the solution becomes clear. Once the solution has cleared, no longer than 5 minutes, 350 µl of Neutralization solution are added and again mixed by gentle inversion several times. The resulting mixture is then centrifuged at 14,000 rpm for 10 minutes to pellet a white precipitate. The supernatant representing the cell lysate is carefully transferred to a fresh Eppendorf tube. 200 µl of the silicon carbide 1000 grade slurry, prepared as above, is added to the tube and mixed therewith by inversion or vortex.

If the plasmid DNA is to be isolated using a pelleting technique the tube is then centrifuged for 1 minute at 14,000 rpm. The resulting supernatant is then aspirated, while taking care not to disturb the silicon carbide pellet. 500 µl of the Wash Solution is added to the pellet and vortexed well. The resulting suspension is again centrifuged for 1 minute at 14,000 rpm. The supernatant is thoroughly aspirated. This washing and centrifugation step is then repeated using a further 500 µl of Wash Solution. The supernatant is again thoroughly aspirated. If the pellet appears to be moist, it can be dried by placing the Eppendorf in a 37° C. oven or even on the benchtop for a few minutes.

100 µl of TE buffer or distilled water warmed to 65°–70° C. are then added to the dried pellet in the Eppendorf and incubated at 65°–70° C. for 1 minute. The Eppendorf tube is then centrifuged at 14,000 rpm for 1 minute. The supernatant, which contains the eluted DNA is carefully pipetted from the resin pellet into a fresh Eppendorf tube. It is important to attempt to transfer as little of the resin into the final preparation as is possible.

If the plasmid DNA is to be isolated using a Spin Column technique the cell lysate and the silicon carbide slurry are mixed by pipetting, then transferred to a spin column filter which has been inserted into a fresh Eppendorf tube. The pore size of the spin column filter should typically be in the range of between 0.22 microns to 0.45 microns, though it can be slightly larger since the average particle size of the silicon carbide 1000 grade is 4.5 microns. The Eppendorf with the spin column is then centrifuged at 14,000 rpm for 30 to 60 seconds. The flow through is discarded and 500 µl of Wash Solution is added to the spin column. The spin column is again centrifuged at 14,000 rpm for 30 to 60 seconds. Again the flow through is discarded and a further 500 µl of Wash Solution added. The spin column is centrifuged at 14,000 rom for 1–2 minutes to ensure the removal of all traces of wash from the spin column. The flow-through is discarded once more and the spin column is then placed in a fresh Eppendorf tube. 100 µl of TE buffer or water warmed to 65°–70° C. is added to the spin column which is subsequently incubated for 1 minute. The spin column is centrifuged at 14,000 rpm for 1 minute. The TE buffer elutes the DNA so that the centrifugation results in eluted DNA being washed through into the Eppendorf tube ready for use.

EXAMPLE 3

Effect of Washing Silicon Carbide 1000 Prior to Use as a DNA Binding Substance

The effect of washing the silicon carbide resin, prior to making the 15% (w/v) slurry, on the digestability of DNA purified in a pellet format was also examined to determine a preferred embodiment. Silicon Carbide 1000 grade was either not washed, washed once, twice or three times with 1M guanidine hydrochloride at room temperature, or distilled water at room temperature or distilled water at 80° C. as outlined in the following protocol:

1. Place 1.5 grams of silicon carbide 1000 grade resin in a 15 ml tube.
2. Suspend the silicon carbide resin in 10 ml of the desired solution (either distilled water or 1M guanidine hydrochloride) and vortex.
3. Place on an aliquot mixer for five minutes.
4. Centrifuge for 5 minutes at 3700 rpm to compact pellet of resin.
5. Discard the supernatant liquid and repeat from step 2 for repeated washes.
6. After the desired number of washes, resuspend the silicon carbide resin in 10 ml of autoclaved distilled water.
7. Isolate plasmid DNA using the protocol outlined above.

Twelve samples of pUC19 DNA were purified using the protocol outlined in Example 2 where the Silicon Carbide resin used for binding DNA varied according to the number of wash cycles it was treated with prior to use. DNA purified using resin prepared from twelve different washes demonstrated digestion with the restriction enzyme Hind III (FIG. 1).

EXAMPLE 4

Scale-up of Purification Protocol

The isolation method disclosed in this invention can be scaled up to accommodate larger quantities of plasmid DNA. The plasmids pUC19 (2686 bp) and pCMV beta (7164 bp) were used in the example protocol described below. The silicon carbide slurry used was 7.5 grams of silicon carbide 1000 grade in 50 ml distilled water or 7M Guanidine Hydrochloride. The protocol followed the identical steps to those outlined in the small scale protocol previously described, though using the amounts of components as listed in Table A.

TABLE 1

Examples of Scale-up

| Culture Volume | Resuspension Buffer | Lysis Buffer | Neutralization Buffer | Silicon Carbide Slurry | TE Buffer | Tube needed |
|---|---|---|---|---|---|---|
| 1.5–3.0 ml | 250 µl | 250 µl | 350 µl | 200 µl | 100 µl | 1.5 ml |
| 50 ml | 4 ml | 4 ml | 4 ml | 3 ml | 500 µl | 50 ml |
| 100–500 ml | 15 ml | 25 ml | 15 ml | 10 ml | 2–4 ml | 250 ml |

DNA purified using scale-up protocols, such as are illustrated in TABLE A, was found to be of comparable quality to small-scale preparations described earlier. However, no simple ratio of components was found to be optimal for scale-up purposes, such that optimization for larger scale preparations will depend upon the culture volume being used.

EXAMPLE 5

Isolation of DNA from Agarose Gel Slices

This example illustrates the isolation of a fragment of DNA from an agarose gel by binding onto Silicon Carbide 1000. The silicon carbide slurry used in this example was 7.5 grams of silicon carbide 1000 grade in 50 ml of 7M guanidine hydrochloride. Two samples of the plasmid pCM- Vbeta (7164 bp) were digested with the restriction enzyme Hind III and loaded onto an agarose gel (1% (w/v) agarose gel in TAE buffer). After electrophoresis, the gel was stained with SYBR Gold and photographed (FIG. 2, left side photo). The 7164 bp bands of pCMV beta were excised from the gel as precisely as possible using a razor blade and DNA was isolated from the agarose slices using the following modification of Example 2:

1. The excised bands were placed in fresh Eppendorf tubes.
2. 400 µl of 7M Guanidine Hydrochloride solution (without resin) was added to the gel slice.
3. The agarose slice was heated at 65° C. until completely melted.
4. 50 µl of silicon carbide 1000 slurry (prepared as in Example 1, described above) was added to the melted agarose.
5. The tube was vortexed well to mix and incubated for 5 minutes at room temperature.
6. The mix was then centrifuged for 1 minute at 14,000 rpm.
7. The supernatant was carefully aspirated.
8. 500 µl Wash Solution was added and the tube was vortexed well.
9. The tube was centrifuged at 14,000 rpm for 1 minute.
10. The wash was carefully aspirated.
11. The wash step was repeated and aspirated as before.
12. The resin was allowed to dry for a few minutes.
13. The DNA fragment was eluted from the resin by adding 50 µl of TE buffer warmed to 65° C.
14. The tube was centrifuged at 14,000 rpm for 1 minute.
15. The eluted DNA was pipeted off the resin and run on an agarose gel (FIG. 2., right side photo).

EXAMPLE 6

Purification of DNA Amplified by PCR

This example illustrates the use of a silicon carbide 1000 slurry (as prepared in Example 1) in the purification of DNA amplified by PCR. The purification protocol begins with a completed PCR reaction in a PCR tube. If mineral oil was used to cap the reaction volume, the aqueous (lower) phase must be carefully removed to a fresh Eppendorf tube. It is to this aqueous phase of the reaction volume that the method of the invention was applied using the following protocol:

1. Add 7M Guanidine Hydrochloride solution to bring volume present in tube to approximately 100 µM.
2. Add 50 µl silicon carbide 1000 slurry (as prepared in Example 1) and vortex to mix.
3. Incubate 5 minutes at room temperature.
4. Centrifuge for 1 minute at 14,000 rpm.
5. Carefully aspirate the supernatant.
6. Wash with 500 µl Wash Solution and vortex to mix.
7. Centrifuge for 1 minute at 14,000 rpm.
8. Carefully aspirate the wash and repeat the wash step.
9. Dry pellet for a few minutes.
10. Elute PCR products with TE buffer warmed to 65° C.
11. Spin at 14,000 rpm for 1 minute and carefully pipet the eluted PCR products into a fresh Eppendorf tube.

PCRs were carried out and a sample of the products was resolved by agarose gel electrophoresis (FIG. 3, left side photo). To the remaining reaction volume, the above protocol was applied and the PCR products isolated were subsequently run on an agarose gel to observe recovery (FIG. 3, right side photo). The results indicate that the PCR products observed on the initial test gel were observed to be isolated using silicon carbide 1000 method. These results demonstrate the protocol's usefulness in separating PCR products from amplification primers, primer-dimers, and enzymes.

EXAMPLE 7

Isolation of Genomic DNA from *E. coli* DH5α

This example illustrates the use of the present invention in the binding and isolation of genomic DNA from *E. coli* DH5α.

1. 1.5 ml of *E. coli* DH5a overnight culture was pelleted for 2 minutes at 10,000 rpm.
2. The pellet was resuspended in 550 µl TE buffer.
3. 30 µl 10% SDS and 30 µl of 20 mg/ml pronase were added.
4. The tubes were mixed gently by inversion and incubated at 37° C. for 1 hour.
5. 100 µl 5M NaCl solution was added and the solution was mixed for a few seconds.
6. An equal volume of Phenol:Chloroform:Isoamyl Alcohol (25:24:1) was added and the solution was mixed gently.
7. The tubes were centrifuged at 11,000 rpm for 5 minutes.
8. The upper phases were collected and an equal volume of Phenol:Chloroform (1:1) was added to each tube and mixed gently.
9. The tubes were centrifuged at 11,000 rpm for 5 minutes and the upper phases were collected in fresh Eppendorf tubes.
10. 200 µl of silicon carbide 1000 slurry was added to each tube and mixed well.
11. The tubes were centrifuged at 14,000 rpm for 1 minute.
12. The supernatant was aspirated from each resin pellet.
13. 500 µl Wash Solution was added to each tube which was then vortexed well to mix.
14. The tubes were centrifuged for 1 minute at 14,000 rpm.
15. The wash was aspirated and repeated once more.
16. The resin pellets were dried at 37° C. for 5 minutes.
17. TE buffer warmed to 65° C. was added to a volume of 200 µl to elute the genomic DNA.

In the above manner, four samples of *E. coli* DH5α genomic DNA were isolated and run on agarose gel (FIG. 4, lanes 1–4). Furthermore, two samples of *E. coli* DH5α genomic DNA were isolated using isopropanol precipitation rather than the silicon carbide method of the invention. These two samples are shown in lanes 5 and 6 of FIG. 4. These results indicate that genomic DNA may be isolated using silicon carbide and that such DNA isolated using the method of this invention is likely to contain less protein contamination than DNA using conventional methods of genomic isolation (note greater amount of proteins in wells 5 and 6 relative to wells 1–4).

EXAMPLE 8

Isolation of RNA Using Silicon Carbide 1000

This example illustrates the capacity of silicon carbide 1000 to bind ribonucleic acids (RNAs). To demonstrate the ability of silicon carbide 1000 to bind RNA, the protocol outlined in Example 2 was carried out without the inclusion of 100 μg/ml RNase A in the Cell Resuspension Solution. In this manner, RNAs liberated from *E. coli* DH5α were not degraded and were isolated in the same fashion as plasmid DNA. This RNA is clearly visible in FIG. 5.

EXAMPLE 9

Isolation of a Range of Plasmid Sizes

This example illustrates that silicon carbide 1000 can be used to isolate plasmids of a range of sizes. Three plasmids (Table B) were isolated from overnight culutres of *E. coli*.

TABLE B

Plasmid Sizes

| PLASMID | SIZE (bp) |
|---|---|
| pUC19 | 2686 |
| pEGFP-N1 | 4733 |
| PCMV beta | 7164 |
| pC BAV-KAN | 36454 |

Following these isolations, plasmids were digested with restriction enyzmes and run on agarose gel (FIG. 6).

EXAMPLE 10

Isolation of DNA Using Silicon Carbide Yields DNA of Quality Comparable to Commercial DNA Purification Kits This example briefly illustrates that plasmid DNA purified using the protocol described in Example 2 is comparable in quality to plasmids isolated using three commercial plasmid purification kits. The plasmid used for these trials was pCMV beta (7164 bp). Following the isolation procedures, each preparation of plasmid was digested with the restriction enzyme Hind III and run with undigested samples on an agarose gel (FIG. 7). Plasmid DNA isolated using silicon carbide 1000 demonstrated complete digestion with Hind III and appeared comparable to plasmid isolated using the three commercial kits used for comparison.

EXAMPLE 11

Transformation of *E. coli* Cells with Silicon Carbide-Purified Plasmid DNA

This example illustrates the transformation of *E. coli* cells with DNA purified using the process presented in Example 2. Two plasmids were used for the transformation procedure: pUC19 and pCMV beta. Details of the results are presented in Table C.

TABLE C

Transformation of E. coli using SiC-purified plasmid DNA

| Plasmid | DNA (ng) | Colonies observed |
|---|---|---|
| pUC19 | 100 | yes |
| pCMV beta | 162 | yes |

Plasmid DNA purified using silicon carbide 1000 was found to be able to confer ampicillin resistance upon *E. coli* cells which previously lacked this genotype.

While only specific embodiments of the invention have been described, it is apparent that various additions and modifications can be made thereto, and various alternatives can be selected. It is, therefore, the intention in the appended claims to cover all such additions, modifications and alternatives as may fall within the true scope of the invention.

Although in the preferred purification method of the invention as described above, a SiC grade of 1000 was used, other grain sites can be used. A range of 600 to 1000 is preferred. It will be readily understood that SiC particles of smaller size provide an overall larger nucleic acid binding surface. However, extremely small particle sizes may result in excessive compacting of the SiC and insufficient mixing with the sample or the washing and elution media.

This invention is useful for isolating nucleotide polymers such as DNA, in a wide range of sizes, and whether the nucleotide polymer is single stranded or double stranded. The invention can be used for the isolation of either RNA or dNA. This simple method involves the principle steps of:

1. immobilizing the nucleotide polymer in the sample into silicon carbide;
2. separating the silicon carbide with the nucleotide polymer immobilized therein from the sample;
3. washing the silicon carbide-bound nucleotide polymer with an ethanol-containing buffer;
4. removing the ethanol-containing buffer; and
5. eluting the nucleotide polymer in a lower salt buffer or water.

What is claimed is:

1. A method for binding a nucleotide polymer to silicon carbide comprising the step of contacting said nucleotide polymer with silicon carbide.
2. The method of claim 1 in which the nucleotide polymer is selected from the group consisting of a DNA oligonucleotide, a DNA polynucleotide, an RNA oligonucleotide, and an RNA polynucleotide.
3. The method of claim 1 in which the nucleotide polymer is a single-stranded chain.
4. The method of claim 1 in which the nucleotide polymer is a double-stranded chain.
5. The method of claim 1 in which the nucleotide polymer is linear.
6. The method of claim 1 in which the nucleotide polymer is circular.
7. The method of claim 2 in which the nucleotide polymer is a single-stranded chain.
8. The method of claim 2 in which the nucleotide polymer is a double-stranded chain.
9. The method of claim 2 in which the nucleotide polymer is linear.
10. The method of claim 2 in which the nucleotide polymer is circular.
11. The method of claim 3 in which the nucleotide polymer is linear.
12. The method of claim 3 in which the nucleotide polymer is circular.
13. The method of claim 4 in which the nucleotide polymer is linear.
14. The method of claim 4 in which the nucleotide polymer is circular.
15. The method of claim 7 in which the nucleotide polymer is linear.
16. The method of claim 7 in which the nucleotide polymer is circular.
17. The method of claim 8 in which the nucleotide polymer is linear.
18. The method of claim 8 in which the nucleotide polymer is circular.

* * * * *